United States Patent [19]

Absil et al.

[11] Patent Number: 4,983,276

[45] Date of Patent: Jan. 8, 1991

[54] OCTANE IMPROVEMENT IN CATALYTIC CRACKING AND CRACKING CATALYST COMPOSITION THEREFOR

[75] Inventors: Robert P. L. Absil, West Deptford; Philip J. Angevine, Woodbury; Robert G. Bundens, Mullica Hill; Joseph A. Herbst, Turnersville, all of N.J.

[73] Assignee: Mobil Oil Corp., Fairfax, Va.

[21] Appl. No.: 471,994

[22] Filed: Jan. 29, 1990

Related U.S. Application Data

[63] Continuation-in-part of Ser. No. 254,524, Oct. 6, 1988, and a continuation-in-part of Ser. No. 98,176, Sep. 18, 1987, abandoned, and a continuation-in-part of Ser. No. 890,268, Jul. 29, 1986, abandoned.

[51] Int. Cl.$^5$ .................................................. C10G 11/05
[52] U.S. Cl. ...................................... 208/120; 502/67; 502/79; 502/214
[58] Field of Search .................... 208/120; 502/67, 79, 502/214

[56] References Cited

U.S. PATENT DOCUMENTS

| | | | |
|---|---|---|---|
| 3,140,249 | 7/1964 | Plank et al. | 208/120 |
| 3,140,251 | 7/1964 | Plank et al. | 208/120 |
| 3,140,252 | 7/1964 | Plank et al. | 208/120 |
| 3,140,253 | 7/1964 | Plank et al. | 208/120 |
| 3,271,418 | 9/1966 | Plank et al. | 208/120 |
| 3,758,403 | 9/1973 | Rosinski et al. | 208/120 |
| 3,769,202 | 10/1973 | Plank et al. | 208/111 |
| 3,894,931 | 7/1975 | Nace et al. | 208/73 |
| 3,894,933 | 7/1975 | Owen et al. | 208/120 |
| 3,894,934 | 7/1975 | Owen et al. | 208/78 |
| 4,309,279 | 1/1982 | Chester et al. | 208/135 |
| 4,309,280 | 1/1982 | Rosinski et al. | 208/120 |
| 4,368,114 | 1/1983 | Chester et al. | 208/120 |
| 4,439,409 | 3/1984 | Puppe et al. | 4239/328 |
| 4,740,292 | 4/1988 | Chen et al. | 208/120 |
| 4,826,667 | 5/1989 | Zones et al. | 423/326 |
| 4,861,741 | 8/1989 | Herbst et al. | 208/120 |
| 4,865,718 | 9/1989 | Herbst et al. | 502/67 |
| 4,898,662 | 2/1990 | Chu et al. | 208/120 |
| 4,898,846 | 2/1990 | Edwards et al. | 502/68 |
| 4,914,067 | 9/1990 | Pellet et al. | 208/120 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/64 |

Primary Examiner—Anthony McFarlane
Attorney, Agent, or Firm—Alexander J. McKillop; Charles J. Speciale; Dennis P. Santini

[57] ABSTRACT

The catalytic cracking of a hydrocarbon oil to provide a product of increased octane number and increased C$_5$+ gasoline content is carried out employing a cracking catalyst composition containing both a large pore crystalline zeolite component and an MCM-22 zeolite component.

21 Claims, No Drawings

OCTANE IMPROVEMENT IN CATALYTIC CRACKING AND CRACKING CATALYST COMPOSITION THEREFOR

CROSS-REFERENCE TO RELATED APPLICATIONS

This application is a continuation-in-part of U.S. patent application Ser. No. 254,524, filed Oct. 6, 1988, pending, which is a continuation-in-part of U.S. patent application Ser. No. 98,176, filed Sept. 18, 1987, now abandoned, which is a continuation-in-part of U.S. patent application Ser. No. 890,268, filed July 29, 1986, now abandoned.

BACKGROUND OF THE INVENTION

This invention relates to improvements in the catalytic cracking of hydrocarbon oils and, in particular, is directed to a process for the catalytic cracking of hydrocarbon oils to produce higher gasoline yields and increased gasoline octane number. The cracking catalyst used herein is a mixture of a large pore crystalline molecular sieve such as zeolite Y and a zeolite referred to herein as zeolite MCM-22.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept adsorption molecules of certain dimensions while rejecting those of large dimensions, these materials nave come to be known as "molecular sieves" are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

The catalytic cracking of hydrocarbon oils utilizing zeolites is a known process, practiced, for example, in fluid-bed catalytic cracking (FCC) units, moving bed or thermofor catalytic cracking (TCC) reactors and fixed bed crackers. Zeolites have been found to be particularly effective for the catalytic cracking of a gas oil to produce motor fuels and have been described and claimed in many patents including U.S. Pat. Nos. 3,140,249; 3,140,251; 3,140,252; 3,140,253; and, 3,271,418. It is also known in the prior art to incorporate the crystalline zeolite into a matrix for catalytic cracking and such disclosure appears in one or more of the above-identified U.S. patents.

It is also known that improved results can be obtained with regard to the catalytic cracking of gas oils if a zeolite having a pore size of less than about 7 Angstrom units, e.g., zeolite A, is included with a crystalline zeolite having a pore size greater than about 8 Angstrom units, e.g., rare earth-treated zeolite X or Y, either with or without a matrix. A disclosure of this type is found in U.S. Pat. No. 3,769,202. Although the incorporation of a crystalline zeolite having a pore size of less than about 7 Angstrom units into a catalyst composite comprising a large pore size crystalline zeolite (pore size greater than about 8 Angstrom units) has indeed been very effective with respect to raising the octane number, it does so at the expense of overall gasoline yield.

Improved results in catalytic cracking with respect to both octane number and overall gasoline yield are disclosed in U.S. Pat. No. 3,758,403. The cracking catalyst comprises a large pore size crystalline zeolite (e.g., pore size greater than about 8 Angstrom units) such as zeolite Y in admixture with a smaller pore zeolite, e.g. ZSM-5, wherein the ratio of smaller pore zeolite to large pore size crystalline zeolite is in the range of 1:10 to 3:1. Effective cracking was achieved when the catalyst was used to obtain the inherent advantages realized in moving bed techniques such as the Thermofor Catalytic Cracking Process (TCC) as well as in fluidized cracking processes (FCC).

The use of zeolites such as ZSM-5 in conjunction with a zeolite cracking catalyst of the X or Y faujasite variety is described in U.S. Pat. Nos. 3,894,931; 3,894,933; and, 3,894,934. The two former patents disclose the use of a ZSM-5 zeolite in amounts of about 5-10 wt. %; the latter patent discloses the weight ratio of ZSM-5 zeolite to large pore size crystalline zeolite within the range of 1:10 to 3:1.

The addition of a separate additive or composite catalyst comprising one or more members of a class of zeolites such as ZSM-5 has been found to be extremely efficient as an octane and total gasoline yield improver when used in very small amounts in conjunction with a conventional cracking catalyst. Thus, in U.S. Pat. Nos. 4,309,279; 4,309,280 and 4,368,114, it was found that only 0.1 to 0.5 wt. % of a ZSM-5 catalyst added to a conventional cracking catalyst under conventional cracking operations could increase octane by about 1-3 RON+O (Research Octane Number Without Lead).

U.S. Pat. No. 4,740,292 discloses a catalytic cracking process which employs a mixture of a faujasite-type zeolite as base cracking catalyst and zeolite Beta. Use of this catalyst mixture results in improved cracking activity, increased octane numbers of the product gasoline and increased gasoline plus alkylate precursor yields relative to the base catalyst alone.

A characteristic of the foregoing catalytic cracking processes, however, lies in their tendency to produce increased $C_3$ and $C_4$ olefins at the expense of $C_5+$ gasoline yield. In those refineries having limited capacity for the conversion of such olefins to more valuable products, e.g., alkylate, it would be desirable to provide a catalytic cracking process which provides a product of increased octane while reducing the aforenoted diminution in $C_5+$ gasoline yield.

SUMMARY OF THE INVENTION

In accordance with the present invention, there has now been discovered an improved process for upgrading total yield and octane number of gasoline boiling range product. This desirable result is obtained by the use of a catalyst composition comprising one or more large pore crystalline molecular sieves in admixture with zeolite MCM-22.

The first component of the catalyst composition employed in the process of the invention is a large pore crystalline molecular sieve, such a material normally having a Constraint Index (as defined in U.S. Pat. No. 4,016,218) less than 1. Large pore crystalline molecular sieves are well known in the art and include faujasite, mordenite, zeolite X, rare earth-exchanged zeolite X (REX), zeolite Y, zeolite Y (HY), rare earth-exchanged zeolite Y (REY), ultrastable zeolite Y (USY), rare earth-exchanged ultra stable zeolite Y (RE-USY), dealuminized Y (DAY), ultrahydrophobic zeolite Y (UHP-Y), dealuminized silicon enriched zeolites such as LZ-210, zeolite ZK-5, zeolite ZK-4, zeolite Beta, zeolite Omega, zeolite L, ZSM-20 and other natural or synthetic zeolites. A more thorough description of faujasite zeolites may be found in Chapter 2 of Breck, Donald W., *Zeolite Molecular Sieves*, Robert E. Krieger Publishing Co., Malabar, Fla., 1984, with specific reference to pages 92-107.

Other large pore crystalline molecular sieves which are useful herein include pillared silicates and/or clays; aluminophosphates, e.g., ALPO-5, VII-5; silicoaluminophosphates, e.g., MCM-9, SAPO-5, SAPO-37, SAPC-31, SAPO-40, SAPO-41; another metal aluminophosphates. These materials are variously described in U.S. Pat. Nos. 4,440,871; 4,554,143; 4,567,029; 4,666,875 and 4,742,033.

The additional component of the catalyst system which is exployed in the cracking process herein, zeolite MCM-22, is a porous crystalline molecular sieve characterized by an X-ray diffraction pattern including values substantially as set forth in Table I, infra.

In carrying out the cracking process of this invention, a suitable hydrocarbon feedstock is heated with the catalyst composition under conversion conditions which are appropriate for cracking. During conversion, the aromatics and naphthenes which are present in the feedstock undergo cracking reactions such as dealkylation, isomerization and ring opening. Additionally, paraffins in the feedstock crack to lower molecular weight species and/or isomerize.

The process of this invention enables heavy feedstocks such as gas oils boiling above about 420° F. to be converted to gasoline range products boiling below about 420° F. and distillates boiling in the 420°-650° F. range. Use of the catalyst composition of this invention results in increased octane numoers of the product gasoline and increased overall gasoline yield relative to that obtained employing large pore crystalline silicate cracking catalysts alone.

DESCRIPTION OF SPECIFIC EMBODIMENTS

The entire contents of applications Ser. Nos. 254,524; 98,176; and 890,268 are incorporated herein by reference.

As mentioned above, the present hydrocarbon conversion process combines elements of cracking and isomerization. The catalyst used in the process comprises a mixture of a large pore (e.g., greater than about 8 Angstroms) crystalline molecular sieve, e.g., faujasite, mordenite, zeolites X, REX, Y, HY, REY, USY, RE-USY, DAY, UHP-Y, LZ-210, ZSM-20, Beta, Omega, L, VPI-5, MCM-9, etc., and the porous crystalline material MCM-22.

Zeolite MCM-22, or simply "MCM-22", appears to be related to the composition named "PSH-3" which is described in U.S. Pat. No. 4,439,409. Zeolite MCM-22 does not appear to contain all of the components which appear to be present in the PSH-3 compositions and is not contaminated with other crystal structures such as ZSM-12 or ZSM-5. In addition, zeolite MCM-22 exhibits unusual sorption capacities and unique catalytic utility when compared to the PSH-3 compositions synthesized in accordance with the procedures described in U.S. Pat. No. 4,439,409.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of omides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations. It can, therefore, be used as a catalyst possessing acid catalysis activity without first having to undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for cracking. These include hydrogen, rare earth metals and metals of Groups IIA, IIIA, IVA, IB, IIB, IIIB, IVB and VIII of the Periodic Table of the Elements. In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined for may be characterized by an X-ray diffraction pattern including the following lines:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstroms Units (A), corresponding to the recorded lines, were determined. In Tables I and II, the relative intensities are given in terms of the symbols W=weak, M=medium, S=strong and VS=very strong. In terms of intensities, these may be generally designated as follows:

W=0–20
M=20–40
S=40–60
VS=60–100

It should be understood that these X-ray diffraction patterns are characteristic of all species of zeolite MCM-22. The sodium form as well as other cationic forms reveal substantially the same pattern with some minor shifts in interplanar spacing and variation in relative intensity. Other minor variations can occur depending on the Y to X, e.g., silicon to aluminum mole ratio of the particular sample, as well as its degree of thermal treatment.

Prior to its use as catalyst, the MCM-22 crystals should be subjected to thermal treatment to remove part or all of any organic constituent present therein.

Zeolite MCM-22, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the catalytic cracking process of this invention, the zeolite MCM-22 crystals can be at least partially dehydrated. This can be achieved by heating the zeolite crystals to a temperature in the range of from about 100° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an omide of trivalent element X, e.g, aluminum, an omide of tetravalent element Y, e.g., silicon, an organic (R) directing agent, hereinafter more particularly described, and water, said reaction mixture having a composition, in terms of mole ratios of omides, within the following ranges:

| Reactants | Useful | Preferred |
|---|---|---|
| $YO_2/X_2O_3$ | 10–60 | 10–40 |
| $H_2O/YO_2$ | 5–100 | 10–50 |

| Reactants | Useful | Preferred |
| --- | --- | --- |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors MCM-22 crystal formation from the above mixture. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM- 22 crystalline material and impurity phases of other crystal structures, e.g., ZSM-12, may be produced.

Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desired to incorporate either or both components of the catalyst system herein with another material which is resistant to the temperatures and other conditions employed in the cracking process of this invention. Such materials include active and inactive materials and other synthetic or naturally occurring porous crystalline molecular sieves as well as inorganic materials such as clays, silica and/or metal omides such as alumina. The latter may be either naturally occurring or in the form of gelatinous precipitates or gels including mixtures of silica and metal omides.

Naturally occurring clays which can be composited with either or both catalyst components herein include the montmorillonite and kaolin family, which families include the subbentonites, and the kaolins commonly known as Dimie, McNamee, Georgia and Floride clays or others in which the main mineral constituent is halloysite, kaolinite, dickite, nacrite, or anaumite. Such clays can be used in the raw state as originally mined or initially subjected to calcination, acid treatment or chemical modification. In addition to the foregoing materials, either or both catalyst components can be composited with one or more porous matrix materials such as silica, alumina, silica-alumina, silica-magnesia, silica-zirconia, silica-thoria, silica-beryllia, silica-titania as well as ternary omide compositions such as silica-alumina-thoria, silica-alumina-zirconia, silica-alumina-magnesia silica-magnesia-zirconia, and the like. It may also be advantageous to provide at least a part of the foregoing matrix materials in colloidal form so as to facilitate extrusion of the bound catalyst component(s).

The relative proportions of catalyst component(s) and binder can vary widely with the content of the former ranging from about 1 to about 95 percent by weight, and more usually from about 10 to about 70 weight percent, of the composite. The large pore crystalline cracking catalyst component and the MCM-22 component can be independently composited with the same or different binder material or both materials can be incorporated together in the same binder material.

The stability of the zeolite catalyst may be increased by steaming, with suitable steam stabilization conditions including contacting the catalyst with, for example, 5–100% steam at a temperature of at least 300° C. (e.g. 300°–650° C.) for at least one hour (e.g. 1–200 hours) at a pressure of 100–2,500 kPa. In a more particular embodiment, the catalyst can be made to undergo steaming with 75–100% steam at 315°–500° C. and atmospheric pressure for 2–25 hours.

The amount of MCM-22 catalyst component which is added to the large pore crystalline cracking catalyst component can be fairly small since the presence of even minor quantities of MCM-22 in the combination catalyst can result in substantial octane gains. As those skilled in the art will appreciate, the exact weight percent of zeolite MCM-22 relative to the total quantity of catalyst component may vary from cracking unit to cracking unit depending upon the desired octane number, total gasoline yield required, the nature of the available feedstock and other similar factors. For many cracking operations, the weight percent of zeolite MCM-22 relative to the total quantity of catalyst composition can range from about 0.01 to about 25 and preferably from about 0.1 to about 10.

The feedstock for the present conversion process comprises a heavy hydrocarbon oil such as a gas oil, coker tower bottoms fraction, reduced crude, vacuum tower bottoms, deasphalted vacuum resids, FCC tower bottoms, cycle oils, and the like. Oils derived from coal, shale or tar sands are also suitable as feedstocks herein. Oils of this kind generally boil about 650° F. (343° C.) although the process is also useful with oils which have initial boiling points as low as 500° F. (260° C.) These heavy oils comprise high molecular weight long-chain paraffins and high molecular weight aromatics with a large proportion of fused ring aromatics. The heavy hydrocarbon oil feedstocks will normally contain a substantial fraction boiling above 450° F. and will normally nave an initial boiling point of about 550° F. (288° C.) and more usually about 650° F.(343° C.). Typical boiling ranges will be about 650° F. to 1050° F. (343° C.-566° C.), or about 650° F. to 950° F. (343° C.-510° C.) but oils with a narrower boiling range may, of course, be processed, for example, those with a boiling range of about 650° F. to 850° F. (343° C. -454° C.). Heavy gas oils are often of this kind as are cycle oils and other nonresidual materials. It is possible to co-process materials boiling below 500° F. out the degree of conversion will be lower for such components. Feedstocks containing lighter ends of this kind will normally have an initial boiling point above about 300° F.

The present process is of a particular utility with highly paraffinic feeds because with feeds of this kind the greatest improvement in octane number can often be obtained. However, benefits can also be achieved with relatively non-waxy feeds.

Processing can be carried out under conditions similar to those used for known types of catalytic cracking processes. Thus, process temperatures of from about 750° F. to about 1200° F. can be used although temperatures above about 1050° F. will normally not be employed. Preferably, temperatures of from about 840° F. to about 1050° F. are employed. The liquid hourly space velocity (LHSV) of the feedstock can generally range from about 0.1 to about 20 hr$^{-1}$ and preferably from about 0.1 to about 10 hr$^{-1}$.

The conversion can be conducted by contacting the feedstock with a fixed stationary bed of catalyst, a fixed fluidized bed or with a transport bed. The catalyst can be regenerated by burning in air or other oxygen-containing gas.

A preliminary hydrotreating step to remove nitrogen and sulfur and to saturate aromatics to naphthenes without substantial boiling range conversion will usually improve catalyst performance and permit lower temperatures, higher space velocities or combinations of these conditions to be employed.

In order to more fully illustrate the present conversion process and the manner of practicing same, the following examples are presented. In examples illustrative of the synthesis of the MCM-22 zeolite catalyst component, whenever sorption data are set forth for comparison of sorptive capacities for water, cyclohexane and/or n-hexane, they are Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha, described in U.S. Pat. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | | |
|---|---|---|
| $SiO_2/Al_2O_3$ | = | 30.0 |
| $OH^-/SiO_2$ | = | 0.18 |
| $H_2O/SiO_2$ | = | 44.9 |
| $Na/SiO_2$ | = | 0.18 |
| $R/SiO_2$ | = | 0.35 | where R is nexamethyleneimine.

The mixture was crystallized in a stainless steel reactor, with stirring, at 150° C. for 7 days to produce the zeolite of the invention. The crystalline product was filtered, washed with water and dried at 120° C. After a 20 hour calcination at 538° C., the X-ray diffraction pattern contained the major lines listed in Table III. The sorption capacities of the calcined zeolite were measured to be:

| | |
|---|---|
| $H_2O$ | 15.2 wt. % |
| Cyclohexane | 14.6 wt. % |
| n-Hexane | 16.7 wt. % |

The surface area of the calcined zeolite was measured to be 494 m$^2$/g.

The chemical composition of the calcined zeolite was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = | 21.1 |

TABLE III

| Degrees 2-Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of zeolite MCM-22 of Example 1 was tested in the Alpha Test and was found to have an Alpha Value of 224.

EXAMPLES 3-5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table IV. The sorption and surface area measurements were of the calcined product.

TABLE IV

| Example | 3 | 4 | 5 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, mole ratio | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

EXAMPLE 6

Quantities of the calcined (538° C. for 3 hours) MCM-22 produced in Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of H$_2$O. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table V:

TABLE V

| Product Composition (uncalcined) | | |
|---|---|---|
| C | 12.1 | wt. % |
| N | 1.98 | wt. % |
| Na | 640 | ppm |
| Al$_2$O$_3$ | 5.0 | wt. % |
| SiO$_2$ | 74.9 | wt. % |
| SiO$_2$/Al$_2$O$_3$, mole ratio | 25.4 | |
| Adsorption, wt. % | | |
| Cyclohexane | 9.1 | |
| n-Hexane | 14.9 | |
| H$_2$O | 16.8 | |
| Surface Area, m$^2$/g | 479 | |

EXAMPLE 8

Twenty-five grams of solid crystal product from Example 7 were calcined in a flowing nitrogen atmospheres at 538° C. for 5 hours, followed by purging with 5% oxygen gas (balance N$_2$) for another 16 hours at 538° C.

Individual 3 g samples of the calcined material were ion-exchanged with 100 ml of 0.1 N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-treated zeolite from Example 8 was sized to 14 to 25 mesh and then calcined in air at 538° C. for 3 hours. The calcined material had an Alpha Value of 173.

EXAMPLE 10

The calcined La-treated material from Example 9 was severely steamed at 649° C. in 100% steam for 2 hours. The steamed zeolite had an Alpha Value of 22, demonstrating that zeolite and very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | | |
|---|---|---|
| $SiO_2/B_2O_3$ | = | 6.1 |
| $OH^-/SiO_2$ | = | 0.06 |
| $H_2O/SiO_2$ | = | 19.0 |
| $K/SiO_2$ | = | 0.06 |
| $R/SiO_2$ | = | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405 $M^2/g$.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 12

A portion of the calcined product of Example 11 was treated with $NH_4Cl$ and again calcined. The final zeolite product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | | |
|---|---|---|
| $SiO_2/B_2O_3$ | = | 12.3 |
| $OH^-/SiO_2$ | = | 0.056 |
| $H_2O/SiO_2$ | = | 18.6 |
| $K/SiO_2$ | = | 0.056 |
| $R/SiO_2$ | = | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 14

A portion of the calcined product of Example 13 was tested in the Alpha Test and found to have an Alpha Value of 5.

EXAMPLE 15

A further sample of the zeolite of the invention was prepared by adding 4.49 parts of hexamethyleneimine to a mixture containing 1.00 parts sodium aluminate, 1.00 parts 50 % NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals were separated from the remaining liquid by filtration, washed with deionized $H_2O$ and dried.

A fluid catalyst was prepared by spray drying an aqueous slurry containing 20 wt. % of the resultant zeolite in a $SiO_2$—/$Al_2O_3$ (87/13 weight ratio) gel matrix and ammonium exchanging the spray dried catalyst. The properties of the fluid catalyst composition, calcined at 650° C. (1200° F.) for 2 hours in air, are set forth in Table VI as follows:

TABLE VI

| Chemical Properties of Dried Catalyst | |
|---|---|
| $Al_2O_3$, wt. % (dry basis) | 9 |
| Na, wt % (dry basis) | 0.07 |
| N, wt % (dry basis) | 1.3 |
| C, wt % (dry basis) | 2.6 |

TABLE VI-continued

| Physical Properties of Calcined Catalyst Density, g/cc | |
|---|---|
| Real | 2.3 |
| Particle | 1.2 |
| Surface Area, m²/g | 314 |
| Pore Volume, cc/g | 0.4 |

Rare earth cations were incorporated into the resultant fluid catalyst by contact with a 1.2 wt. % rare earth chloride solution (Davision Specialty Chemical Co.) for 6 hours at room temperature. The wt. % of each rare earth methal present in the solution was as follows: praseodymium, 1.16; neodymiium, 4.05; lanthanum, 5.53; cerium, 9.41; and, semarium, 0.68. After filtering, the rare earth-treated catalyst was washed free of chloride and dried at 120° C. (250° F.). The resulting rare earth-treated fluid catalyst, which was calcined at 540° C. (1000° F.) for 2 hours in air, possessed the properties set forth in Table VII as follows:

TABLE VII

| Chemical Properties | |
|---|---|
| Rare Earth Oxide, wt % (dry basis) | 2.4 |
| Al₂O₃, wt % (dry basis) | 10 |
| Na, wt % (dry basis) | 0.01 |
| Physical Properties Density, g/cc | |
| Real | 2.3 |
| Particle | 1.2 |
| Surface Area, m²/g | 309 |
| Pore Volume, cc/g | 0.4 |

EXAMPLE 16

Mixtures of regenerated equilibrium REY catalyst (Engelhard HEZ-53) as a base cracking catalyst, the catalyst compositions of Example 15, and a ZSM-5 zeolite were prepared as follows:

| Base Catalyst | Additive | Catalyst Composition |
|---|---|---|
| REY | — | A |
| REY | calcined catalyst of Example 15 (0.5 wt % zeolite) | B |
| REY | calcined catalyst of Example 15 steamed at 1450° F. (790° C.) for 10 hours at 0 psig (100 kPa) in 45% steam/55% air (5 wt % zeolite) | C |
| REY | rare earth-treated catalyst of Example 15 (0.5 wt. % zeolite) | D |
| REY | rare earth-treated catalyst of Example 15 steamed at 1450° F. (790° C.) for 10 hours at 0 psig (100 kPa) in 45% steam/55% air (5 wt % zeolite) | E |
| REY | 25% ZSM-5 additive catalyst steamed at 1450° F. (790° C.) for 10 hours at 0 psig (100 kPa) in 45% steam/55% air (2 wt % ZSM-5) | F |

Catalyst compositions A-F were evaluated for cracking a heavy gas oil in a fixed-fluidized bed unit at 960° F. (515° C.) over a range of catalyst/oil ratios. The heavy gas oil possessed the properties set forth in Table VIII as follows:

TABLE VIII

| Properties of Heavy Gas Oil Feed | |
|---|---|
| Gravity, API | 24.3 |
| Aniline Pt., °F. | 177 |
| Hydrogen, wt. % | 12.3 |
| Sulfur, wt. % | 1.87 |
| Nitrogen, wt. % | 0.10 |
| Basic Nitrogen, ppm | 327 |
| Conradson Carbon, wt. % | 0.28 |
| Kinematic Viscosity at 210° F. | 3.6 |
| Bromine No. | 4.2 |
| R.I. at 70° F. | 1.5080 |
| Molecular Weight | 358 |
| Pour Point, °F. | 85 |
| Paraffins, wt. % | 23.5 |
| Naphthenes, wt. % | 32.0 |
| Aromatics, wt. % | 44.5 |
| Aromatic Carbon, wt. % | 18.9 |
| Ni, ppm | 0.3 |
| V, ppm | 0.6 |

The performance of the various catalyst compositions at 65 vol. % conversion are shown in Table IX and yield/octane shifts for catalyst compositions B-F are shown in Table X as follows:

TABLE IX

Performance of Catalysts A-F for Cracking Heavy Gas Oil

| | Catalyst Composition | | | | | |
|---|---|---|---|---|---|---|
| | A | B | C | D | E | F |
| Conversion, % Vol | 65.0 | 65.0 | 65.0 | 65.0 | 65.0 | 65.0 |
| Conversion, % Wt | 62.8 | 63.6 | 62.7 | 62.6 | 62.8 | 62.8 |
| C₅⁺, Gasoline, % Vol | 50.6 | 46.3 | 49.6 | 46.3 | 49.3 | 47.5 |
| C₅⁺, Gasoline, % Wt | 41.8 | 38.1 | 40.7 | 38.3 | 40.5 | 39.1 |
| Total C₄, % Vol | 14.2 | 18.4 | 15.8 | 16.3 | 15.1 | 15.8 |
| Dry Gas, % Wt | 7.4 | 9.1 | 7.4 | 8.9 | 8.0 | 8.9 |
| Coke, % Wt | 4.54 | 4.76 | 4.60 | 5.09 | 4.72 | 4.52 |
| C-On-Cat, Final, % Wt | 0.94 | 1.18 | 0.95 | 1.10 | 0.87 | 0.91 |
| N—C₅, % Vol | 0.4 | 0.6 | 0.7 | 0.4 | 0.5 | 0.4 |
| I—C₅, % Vol | 4.1 | 5.0 | 4.7 | 5.0 | 4.8 | 4.6 |
| C₅⁼, % Vol | 3.6 | 4.2 | 4.0 | 4.4 | 4.2 | 4.6 |
| N—C₄, % Vol | 1.0 | 1.2 | 1.1 | 1.0 | 1.3 | 1.0 |
| N—C₄, % Wt | 0.7 | 0.7 | 0.7 | 0.6 | 0.8 | 0.6 |
| I—C₄, % Vol | 6.2 | 7.8 | 6.9 | 7.4 | 6.6 | 6.6 |
| I—C₄, % Wt | 3.8 | 4.8 | 4.2 | 4.5 | 4.0 | 4.0 |
| C₄⁼, % Vol | 7.0 | 9.4 | 7.8 | 7.9 | 7.2 | 8.2 |
| C₄⁼, % Wt | 4.6 | 6.2 | 5.1 | 5.2 | 4.8 | 5.4 |
| C₃, % Vol | 1.8 | 2.0 | 1.9 | 2.2 | 2.0 | 2.1 |
| C₃, % Wt | 1.0 | 1.1 | 1.0 | 1.2 | 1.1 | 1.1 |
| C₃⁼, % Vol | 6.9 | 9.7 | 7.3 | 9.4 | 7.8 | 9.1 |
| C₃⁼, % Wt | 3.9 | 5.5 | 4.2 | 5.3 | 4.4 | 5.1 |
| C₂, % Wt | 0.5 | 0.4 | 0.5 | 0.4 | 0.5 | 0.5 |
| C₂⁼, % Wt | 0.5 | 0.5 | 0.5 | 0.5 | 0.5 | 0.6 |
| C₁, % Wt | 0.5 | 0.5 | 0.5 | 0.5 | 0.5 | 0.6 |
| H₂, % Wt | 0.18 | 0.16 | 0.18 | 0.18 | 0.20 | 0.20 |
| H₂S, % Wt | 0.78 | 0.90 | 0.49 | 0.80 | 0.75 | 0.76 |
| Hydrogen Factor | 137 | 134 | 143 | 140 | 147 | 140 |
| Potential Alkylate, % Vol | 23.1 | 31.7 | 25.2 | 28.8 | 25.0 | 28.8 |
| C₅⁺ Gasoline + Potential Alkylate, % Vol | 73.7 | 78.0 | 74.8 | 75.1 | 74.3 | 76.3 |
| Outside I—C₄, % Vol | 9.5 | 13.7 | 10.2 | 12.2 | 10.4 | 13.0 |
| RON + O, C₅⁺ Gasoline | 89.5 | 91.2 | 90.3 | 90.6 | 90.5 | 90.8 |
| RON + O, C₅⁺ Gasoline + Potential Alkylate | 90.9 | 92.3 | 91.6 | 91.9 | 9.16 | 92.0 |
| LFO, % Wt | 30.4 | 29.8 | 29.9 | 31.0 | 30.7 | 30.1 |
| HFO, % Wt | 6.8 | 6.6 | 7.4 | 6.3 | 6.5 | 7.1 |
| G + D, % Wt | 72.2 | 67.9 | 70.6 | 69.3 | 71.2 | 69.1 |

TABLE X

Yield/Octane Shifts for Catalyst Compositions B-F With Respect to Catalyst Composition A

| | Catalyst Composition | | | | |
|---|---|---|---|---|---|
| 65 Vol % Conversion | B | C | D | E | F |
| —ΔC₅⁺ gasoline, Vol % | 4.3 | 1.0 | 4.3 | 1.3 | 3.1 |
| ΔRON + O | 1.7 | 0.8 | 1.1 | 1.0 | 1.3 |
| ΔC₃⁼ + C₄⁼ + iC₄, Vol % | 6.8 | 1.9 | 4.6 | 1.5 | 3.8 |

TABLE X-continued

Yield/Octane Shifts for Catalyst Compositions B-F With Respect to Catalyst Composition A

| 65 Vol % Conversion | Catalyst Composition | | | | |
|---|---|---|---|---|---|
| | B | C | D | E | F |
| $-\Delta G + D$ | 4.3 | 1.8 | 3.0 | 1.2 | 3.1 |
| $-\Delta C_5^+$ gasoline/$\Delta RON + O$ | 2.5 | 1.3 | 3.9 | 1.3 | 2.4 |

As shown in Tables IX and X, compared to catalyst composition A (REY alone), catalyst compositions B and D (catalyst mixtures containing 0.5 wt % unsteamed zeolite MCM-22 and unsteamed rare earth-exchanged zeolite MCM-22, respectively) produced $C_5\pm$ gasoline with a 1 to 2 RON boost with some loss in $C_5+$ gasoline and a corresponding increase in $C_3$ and $C_4$ olefins and isobutane. All three steamed catalyst compositions (C, E and F) produced $C_5+$ gasoline with a 0.8 to 1.3 RON boost, a loss in $C_5+$ gasoline and a corresponding increase in $C_3$ and $C_4$ olefins and isobutane. However, compared to catalyst composition F (containing ZSM-5), catalyst compositions C and E (containing zeolite MCM-22) were found to be substantially more selective since the loss in $C_5+$ gasoline per unit octane increase (1.3) considerably less, for catalyst compositions C. and E than for catalyst composition F (2.4).

What is claimed is:

1. A catalytic cracking process which comprises catalytically cracking a hydrocarbon feed with a cracking catalyst composition comprising as a first component, a large pore crystalline molecular sieve and as a second component, a porous crystalline material characterized by an X-ray diffraction pattern including values substantially as set forth in Table I of the specification.

2. The process of claim 1 wherein the second component is characterized by an X-ray diffraction pattern including values substantially as set forth in Table II of the specification.

3. The process of claim 1 wherein the second component has a composition comprising the molar relationship $$X_2O_3:(n)YO_2,$$

wherein n is at least about 10, X is a trivalent element and Y is a tetravalent element.

4. The process of claim 1 wherein the second component possesses equilibrium adsorption capacities of greater than about 4.5 wt. % for cyclohexane vapor and greater than about 10 wt. % for n-hexane vapor.

5. The process of claim 3 wherein X is selected from the group consisting of aluminum, boron, gallium and combinations thereof and Y is selected from the group consisting of silicon, germanium and combinations thereof.

6. The process of claim 3 wherein X comprises aluminum and Y comprises silicon.

7. The process of claim 1 wherein the first component, second component or mixture thereof is a rare earth treated material.

8. The process of claim 1 wherein said catalyst has been thermally treated at a temperature up to about 925° C. in the presence or absence of steam.

9. The process of claim 1 wherein the second component comprises from about 0.01 to about 25 wt % of the total cracking catalyst composition.

10. The process of claim 1 wherein the second component comprises from about 0.1 to about 10 wt % of the total cracking catalyst composition.

11. The process of claim 1 wherein the first component is selected from the group consisting of zeolite X, zeolite Y, USY, dealuminated X, dealuminated Y, dealuminated USY, dealuminated-silicon-enriched zeolite X, dealuminated-silicon-enriched zeolite Y, dealuminated-silicon-enriched USY and admixtures thereof.

12. The process of claim 1 wherein the first component is USY.

13. The process of claim 1 wherein the first component is selected from the group consisting of Zeolite Omega, ZSM-20, mordenite, Zeolite Beta, Zeolite L, and admixtures thereof.

14. The process of claim 1 wherein the large pore crystalline molecular sieve comprises a silicoaluminophosphate selected from the group consisting of MCM-9, SAPO-5, SAPO-37, SAPO-31, SAPO-40, SAPO-41 and admixtures thereof.

15. The process of claim 1 wherein the large pore crystalline molecular sieve comprises an aluminophosphate selected from the group consisting of ALPO- 5 and VIP-5.

16. The process of claim 1 wherein the large pore molecular sieve has a Constraint Index of less than 1.

17. The process of claim 1 wherein the first component, second component or mixture thereof is combined with a binder material.

18. The process of claim 1 wherein the first and second components are combined together with a binder material.

19. The process of claim 1 wherein said cracking is carried out in a moving bed.

20. The process of claim 1 wherein said cracking is carried out under fluid catalytic cracking conditions.

21. The process of claim 1 wherein the hydrocarbon feed is at least one heavy hydrocarbon oil selected from the group consisting of gas oil, coker tower bottoms fraction, reduced crude, vacuum tower bottoms, deasphalted vacuum resids, fluidized catalytic cracking tower bottoms, cycle oils, oil derived from coal, oil derived from shale and oil derived form tar sands.

* * * * *

UNITED STATES PATENT AND TRADEMARK OFFICE
CERTIFICATE OF CORRECTION

PATENT NO. : 4,983,276

DATED : 1/8/91

INVENTOR(S) : R.P.L. Absil et al

It is certified that error appears in the above-identified patent and that said Letters Patent is hereby corrected as shown below:

Title page, list of inventors, add --Sadi Mizrahi and Mae K. Rubin--

Signed and Sealed this

Twelfth Day of May, 1992

*Attest:*

DOUGLAS B. COMER

*Attesting Officer*     *Acting Commissioner of Patents and Trademarks*